ns
United States

Lezdey

4,542,019

Sep. 17, 1985

[54] ANTACID COMPOSITIONS

[76] Inventor: John Lezdey, 976 Kingston Dr., Cherry Hill, N.J. 08034

[21] Appl. No.: 474,288

[22] Filed: Mar. 11, 1983

[51] Int. Cl.[4] ..................... A61K 33/06; A61K 33/08; A61K 33/10

[52] U.S. Cl. ...................................... 424/157; 424/38; 424/154; 424/156; 424/158

[58] Field of Search ................... 424/156, 157, 158, 38

[56] References Cited

U.S. PATENT DOCUMENTS

| | | | |
|---|---|---|---|
| 3,264,097 | 8/1966 | Weiss | 75/67 |
| 3,539,306 | 11/1970 | Kumura et al. | 23/315 |
| 4,239,754 | 12/1980 | Sache et al. | 424/183 |
| 4,356,167 | 10/1982 | Kelly | 424/38 |
| 4,369,182 | 1/1983 | Ghyczy et al. | 424/199 |

OTHER PUBLICATIONS

*Gastroenterology*, 82, 1115, (1982), Role of Phospholipids in the Gastric Mucosal Barrier.
*Chemical Abstracts*, vol. 91, (1979), 163005y.

*Primary Examiner*—Frederick E. Waddell

[57] ABSTRACT

A composition of matter of the combination of an antacid and liposome, wherein the antacid is retained on or in the liposome and the lipids of said liposome are formed on non-toxic physiologically acceptable and metabolizable phospholipids, and the antacid prepartions thereof.

9 Claims, No Drawings

ANTACID COMPOSITIONS

This invention relates to a novel composition of matter containing an antacid, and the use therefor. More particularly, this invention relates to an improvement in antacid compositions containing magnesium aluminate hydrate type substances.

Magnesium aluminate hydrate substances including hydrotalcites, magaldrate, magnesium hydroxide-aluminum hydroxide combinations, and such substances with carbonate, sulfate and phosphate ions are well known in tablet form and in suspensions for the treatment of peptic ulcers, esophagitis, and other acute or chronic gastric or duodenal disturbances associated with mucosal irritations caused by gastric juices. However, the commercial antacid preparations are not suitable for treating duodenal ulcers or irritations since they become inactive prior to reaching the duodenum unless taken in large excesses which then causes constipation or other gastric irritation.

It is also recognized that the conventional antacid preparations may cause calcium depletion in the human body. Addition of phosphate ions to the formulations has been proposed to remedy this problem.

It is further known that stress, particularly "executive stress" may cause gastric irritations which may result in ulcers or aggravation of an ulcer condition. In addition, stress also causes platelet aggregation which may lead to thrombosis, and other stress symptoms. Conventional antacid formulations are intended to relieve only the gastric irritations and play no role in stress management or with regard to prevention of thrombosis.

U.S. Pat. No. 3,264,097 to B. Lomberg, which is incorporated herein by reference, relates to the preparation of magaldrate, one of the magnesium aluminate hydrates useful in the present invention.

U.S. Pat. No. 3,539,306 to Kumura et al discloses synthetic hydrotalcites which may be utilized in connection with this invention.

U.S. Pat. No. 4,239,754 to Sache et al, which is incorporated herein by reference, discloses a process for retaining heparin in or on liposomes.

U.S. Pat. No. 4,356,167 to Lawrence A. Kelly, which is incorporated herein by reference, relates to a liposome drug delivery system.

An objective of the invention is to overcome prior antacid disadvantages and in addition provide stress management including prevention of platelet aggregation.

A further object of the invention is to provide an antacid preparation which can treat irritations in the duodenum.

A still further objective of the invention is to provide a prolonged duration of antacid action.

The preparation of the invention consists essentially of liposomes with an antacid retained therein or thereof.

The invention further relates to dispersions of liposomes of that type in a liquid, particularly an aqueous vehicle. It also relates to pharmaceutical compositions containing said preparation or dispersions associated whenever necessary to a pharmaceutical vehicle enabling its adminstration.

Liposomes prepared from phospholipids, or from certain other lipid substances of hydrophobic fatty materials have already been described. The liposomes are constituted by hydrated lipid crystals, generally mono or multi layered (or uni- or multi- lamellar) dispersed or disperable in an aqueous medium, with a part of the aqueous medium from which the crystals were produced being trapped in the vesicles formed as a result of the capacity of their lipids or fatty materials to undergo "swelling" in aqueous medium, especially under the effect of an agitation or of ultra-sonic radiation. These liposomes can also be described as being formed or one of a series of concentric bi-layers of the lipids, alternating with aqueous compartments. When the aqueous solution from which the liposomes were formed is or contains at least a partial solution of an antacid, then a part of this antacid solution is retained by and in the interstices of the liposomes to form the compositions of this invention.

The invention also provides a process for preparing liposomes retaining an antacid which process comprises subjecting a dispersion of physiologically acceptable lipids of the type capable of forming liposomes, preferably phospholipids, in at least a partial solution an aqueous one, to stirring or preferably to ultrasonic action (or sonication) until liposomes are formed which retain a part at least of the antacin initially contained in the aqueous solution.

Any non toxic physiologically acceptable and metabolizable lipid, capable of forming liposomes, may be suitably used for carrying out the invention.

Phospholipids form an important class of said suitable lipids, the phospholipids having the formula

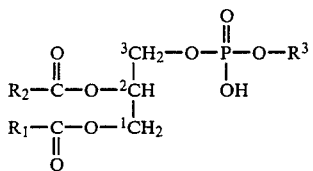

wherein $R_1$ and $R_2$ are derived from fatty acids, for instance those which comprise from 4 to 22, and $R_3$ is part of an ester group, which in preferred instances is that which results from the esterification of the phosphoryl group of said phospholipid, by an amino-alcohol such as choline (2-hydroxyethyltrimethyl-ammonium hydroxide), ethanol-amine, serine, etc. or by a sugar derivative comprising an ol function, such as inositol for instance. Other lipids more or less closely related to phospholipids and capable of forming liposomes, are also suitable for the invention. Among these one should cite, in a non limitative manner, particularly plasmalogens, gangliosides, sphingolipids, phosphoglycerides, phosphonolipids (particularly those which differ from the phospholipids of the above formula in that a —CH$_2$—CH$_2$—NH$_3$+group is substituted for the —OR$_3$ group. ("LIPID BIOCHEMISTRY, An introduction" M. I. GURR and A. T. JAMES, 2nd edition, 1875, Chapman and Hall, London) and the sodium or potassium salts thereof.

Other examples of useful lipids are those formed of fatty acids comprising long non-saturated hydrocarbon chains, such as those designated as "ufasomes" and described by GEBICKI and HICKS; Chemistry and Physics of Lipids, 1976, Vol. 16, pages 142-160, or of monoacylated compounds, comprising chains derived of fatty acids having eight or more carbon atoms as well as non toxic anionic and cationic pharmaceutically acceptable detergents, all of the type disclosed by W. R. HARGREAVES and D. W. DEAMER, "CONFER- ENCE ON LIPOSOMES AND THEIR USES IN BIOLOGY AND MEDICINE", Sept. 14–16, 1977, New York Academy of Sciences, etc.

Preferred classes of lipids, among which phospholipids, for use in the present invention, are those which comprise non-saturated fatty acid chains, such as those which comprise from 18 and 20 carbon atoms, and at least one non-saturated bond.

These antacid containing liposome preparations which are formed starting from lipids, more particularly phospholipids having non saturated fatty-acid chains, advantageously derived of essential fatty acids, are of particular interest owing to the complementary therapeutical properties of said phospholipids themselves, which are of particular compatibility (often a particularly desirable one) with those of the antacid.

More particularly phosphatidylcholines are known to possess, among other valuable therapeutical properties, a protecting action against degenerative atheromatous processes or phenomena, to reduce capillary permeability and veinous toxicity, to prevent sludge formation in the capillary system and to decrease platelets hyperadhesivity and hyperaggregability.

They are further capable of restoring a proper balance between non-saturated and saturated fats, insofar as the latter are often in excess in the organism of those patients who suffer from vascular or cardiovascular diseases.

For carrying out the process according to the invention, conventional technology and equipment can be resorted to. This applies particularly to the use of sonication, which can be carried out for instance with the equipment comprising metallic probes introduced into the dispersion which is to be subjected to sonication. The ultimate nature and sizes of the phospholipidic vesicles will, as is well known, depend upon the time and intensity of sonication, the type of the lipods used, the ionic strength of the medium, the temperature, etc. As far as the technics are concerned, reference can, for instance, be had to chapter IV of METHODS IN CELL BIOLOGY edited by David M. Prescott, volume XIV, 1976, Academic Press, New York, Page 33.

Advantageously, the initial dispersion is obtained from a thin film of lipid formed in the vessel intended to contain the final product, this thin film preferably being obtained by introducing a solution of the appropriate lipids into the vessel and then evaporating the solvent therefrom. The antacid solution may then be introduced into the vessel whereby a dispersion of the lipids in the solution of antacid is formed, by stirring, which dispersion can then be subjected to ultrasonic radiation to obtain the above-indicated result.

In a first stage, there is formed a suspension of swollen liposomes having a milky aspect, the liposomes of which are then believed to be essentially formed of a series of concentric lipid bi-layers alternating which aqueous compartments in which antacid is retained.

The liposomes so obtained may be separated from the aqueous medium for example by centrifugation. The liposomes contained in the sediment may then be washed if desired so as to eliminate any active substance not incorporated into the liposomes. The liposomes may then be taken up in a buffer and stored, desirably in the cold and preferably at a temperature of +4° C. Liposomes stored in this manner are stable over prolonged periods of time.

It has however been found that liposomes can be obtained which retain even greater amounts of antacid upon controlling and prolonging the conditions of stirring, particularly sonication, so as to provide smaller liposomes, particularly unilamellar vesicles within the starting aqueous solution of antacid. It is not necessary for the present invention that all of the antacid be retained in this liposome since only a part is required for action in the duodenum.

It is also not necessary for achieving the advantages of the invention that only liposome-antacids be utilized or separated but only that it form at least part of the total antacid preparation, preferably about 10%.

The antacid portion of this composition may be, for example, hydrotalcite type substances, magnesium hydroxide-aluminum hydroxide combinations, magaldrate, tagamet, and such substances with carbonate, sulfate and/or phosphate ions.

The following Examples serve to demonstrate the compositions and preparations of the invention.

EXAMPLE I

Following the procedure of U.S. Pat. No. 4,239,754, a lipid phase made up of the three components lecithin, cholesterol and dicetyl-phosphate in a molar ration of 7:2:1 is prepared with 2.6 g of lecithin, 0.04.4 g of cholesterol and 0.31 g dicetyl-phosphate by dissolving in 50 ml of chloroform and the solution evaporated, 4.0 g of magaldrate is dissolved in 50 ml of an acid buffer (citric acid) pH7.5–8.0 and added to the phospholipids. The mixture is then subjected to sonification for 10 seconds. The precipitate was then evaporated and added to a commercially prepared aluminum hydroxide-magnesium hydroxide suspension (Maalox, a product of William H. Rorer Inc.).

In place of cholesterol, any sterol capable of forming liposomes may be utilized, such as, desmosterol, estradiol, B-sitosterol, and the like.

EXAMPLE II

Following the procedure of Example I, two lipid phases are made up. Into one lipid phase is added 5.0 g of aluminum hydroxide gel dissolved in a phosphate buffer. In the other lipid phase, 1.0 g of magnesium hydroxide dissolved in a phosphate buffer. After sonification and evaporation the powder is admixed with 5% simethicone and formed into tablets.

EXAMPLE III 10,000 units of an antacid suspension, where each unit contains 500 mg of liposome-antacid 5 ml of suspension, are prepared as follows:

| | |
|---|---|
| magaldrate-liposome | 5000 g |
| 70% aqueous sorbitol solution | 5000 g |
| Sodium carboxymethyl cellulose, 400 cp/2% | 650 g |
| Sodium salt of methyl-p-hydroxybenzoate | 112.5 g |
| Sodium salt of propyl-p-hydroxybenzoate | 12.5 g |
| Sodium salt of saccharin | 50 g |
| Anethole | 20 g |
| Water q.s. | 50 l |

Sodium carboxymethyl cellulose, sodium methyl hydroxybenzoate, sodium propyl hydroxybenzoate and the sodium salt of saccharin are dissolved with stirring in 35 liters of distilled water. The sorbitol solution is added, and the magaldrate-liposome was dispersed in the solution. Subsequently, anethole was added, and the mixture was diluted to 50 liters with water. The resulting suspension was made to pass through a colloid mill and then packaged as single doses in containers, with each container holding 5 ml of suspension.

The formulation can be used to treat duodenum irritations.

EXAMPLE IV 10,000 antacid tablets were prepared, each containing 500 mg of a hydrotalcite-liposome of the present invention:

| | |
|---|---|
| $Mg_6Al_2(OH)_{14}CO_3HPO_44H_2O$—liposome | 5000 g |
| Mannitol | 6000 g |
| Cornstarch | 195 g |
| Soluble starch | 325 g |
| Fructose | 20 g |
| Flavor (dry powder) | 10 g |
| Magnesium stearate | 100 g |

The hydrotalcite-liposome and mannitol are mixed and granulated with a solution of the fructose and the soluble starch in 6 liters of water. The granulate was dried and subsequently screened through a screen with a mesh size of 0.5 mm. The granulate was then mixed with the remainder of the compounds, and the mixture was pressed to tablets of 1.165 g using a 15 mm disk and a flat bevel-edged die.

EXAMPLE V 10,000 swallow tablets were prepared, each containing 500 mg of a antacid per tablet:

| | |
|---|---|
| magaldrate-liposome | 2000 g |
| magaldrate | 3000 g |
| Cornstarch | 195 g |
| Soluble Starch | 325 g |
| Magnesium Stearate | 100 g |

The two antacids and corn starch are mixed and granulated with a solution of soluble starch in 6 liters of water. The granulate is dried and subsequently screened through a screen with a mesh size of 0.5 mm. The granulate is then mixed with the magnesium stearate, and the mixture is pressed to tablets of 0.562 using a 10 mm disk and a flat bevel-edged die.

The formulation can be used for treatment of duodenal irritations and excess acid and pepsin secretions.

What is claimed is:

1. A method for treating patients suffering from duodenal disturbances caused by gastric juices which comprises administering to said patient an effective amount of an antacid and liposome, wherein the antacid is retained on or in the liposome and the lipids of said liposome are formed of non-toxic physiologically acceptable and metabolizable phospholipids.

2. The method of claim 1 wherein the antacid is trapped within the lipid vesicles of the liposomes.

3. The method of claim 1 wherein the lipids are phospholipids.

4. The method of claim 3 wherein the lipid is lecithin.

5. The method of claim 1, wherein the lipids are selected from the group consisting of
   plasmalogens,
   gangliosides,
   sphingolipids,
   phosphoglycerides,
   phosphonolipids,
   ufasomes and
   monoacylated compounds of fatty acid
chains having at least 8 carbon atoms and non-toxic anionic or cationic pharmaceutically acceptable detergents.

6. The method of claim 4 wherein said phospholipids comprise phosphatidylcholines of which at least one of the fatty acyl groups is an unsaturated fatty acyl group.

7. The method of claim 1 wherein said antacid is a magnesium aluminate hydrate.

8. The method of claim 1 wherein said antacid is a balance of magnesium hydroxide and aluminum hydroxide.

9. The method of claim 1 wherein said antacid is selected from the group consisting of magaldrate, hydrotalcite and magnesium hydroxide-aluminum hydroxide.

* * * * *